United States Patent
Yamada

(10) Patent No.: US 10,896,760 B2
(45) Date of Patent: Jan. 19, 2021

(54) ESTIMATION OF MUSCLE ACTIVITIES USING THE MUSCLES RELATIONSHIP DURING SIMULATING MOVEMENTS

(71) Applicant: INTERNATIONAL BUSINESS MACHINES CORPORATION, Armonk, NY (US)

(72) Inventor: Yasunori Yamada, Saitama (JP)

(73) Assignee: International Business Machines Corporation, Armonk, NY (US)

( * ) Notice: Subject to any disclaimer, the term of this patent is extended or adjusted under 35 U.S.C. 154(b) by 416 days.

(21) Appl. No.: 15/725,596

(22) Filed: Oct. 5, 2017

(65) Prior Publication Data

US 2019/0108319 A1 Apr. 11, 2019

(51) Int. Cl.
| | |
|---|---|
| *G06F 30/00* | (2020.01) |
| *G16H 50/50* | (2018.01) |
| *G06F 7/22* | (2006.01) |
| *G06F 111/10* | (2020.01) |
| *G06F 30/17* | (2020.01) |

(52) U.S. Cl.
CPC ............ *G16H 50/50* (2018.01); *G06F 7/22* (2013.01); *G06F 30/00* (2020.01); *G06F 30/17* (2020.01); *G06F 2111/10* (2020.01)

(58) Field of Classification Search
USPC ............... 600/546; 703/2, 5; 607/48; 434/1
See application file for complete search history.

(56) References Cited

U.S. PATENT DOCUMENTS

| | | | |
|---|---|---|---|
| 7,251,593 B2 | 7/2007 | Dariush et al. | |
| 7,308,826 B2 | 12/2007 | Nakamura et al. | |
| 9,078,585 B2 | 7/2015 | Miyazaki et al. | |
| 10,507,121 B1 | 12/2019 | Hoffmann et al. | |
| 10,676,083 B1 | 6/2020 | De Sapio et al. | |
| 2007/0172797 A1* | 7/2007 | Hada | G09B 23/32 434/1 |
| 2007/0256494 A1 | 11/2007 | Nakamura et al. | |
| 2011/0105962 A1 | 5/2011 | Ochi et al. | |

(Continued)

FOREIGN PATENT DOCUMENTS

| | | |
|---|---|---|
| CN | 102112183 A | 6/2011 |
| JP | 2010029340 A | 2/2010 |

OTHER PUBLICATIONS

Nakashima, M. et al., "3D-CG based musculoskeletal simulation for a swimmer wearing competitive swimwear" Procedia Engineering (May 2013) pp. 367-372, vol. 60.

(Continued)

*Primary Examiner* — Thai Q Phan
(74) *Attorney, Agent, or Firm* — Tutunjian & Bitetto, P.C.; Randall Bluestone

(57) ABSTRACT

A technique for estimating activity of a plurality of muscles is disclosed. In this technique, for each of two or more muscles included in a musculoskeletal body model, a set of time-series data of muscle state change that accompanies motion of a body is acquired. A correlation between the sets of time-series data for a pair of muscles included among the two or more muscles is calculated. An activity of a plurality of muscles included in the musculoskeletal body model in a motion state that is an estimation target is estimated using an objective function including a constraint using the correlation of the sets of time-series data.

20 Claims, 4 Drawing Sheets

(56) References Cited

U.S. PATENT DOCUMENTS

| | | | | |
|---|---|---|---|---|
| 2012/0172745 A1* | 7/2012 | Miyazaki | ............. | A61B 5/0488 600/546 |
| 2016/0203620 A1* | 7/2016 | Zou | ........................ | A61B 6/032 378/19 |
| 2016/0206225 A1 | 7/2016 | Todorov et al. | | |
| 2016/0207201 A1* | 7/2016 | Herr | ..................... | B62D 57/032 |

OTHER PUBLICATIONS

Murai, A. et al., "Musculoskeletal Modeling and Physiological Validation" 2014 IEEE Workshop on Advanced Robotics and its Social Impacts (ARSO) (Sep. 2014) pp. 108-113.

Bovi, G. et al., "A multiple-task gait analysis approach: Kinematic, kinetic and EMG reference data for healthy young and adult subjects" Gait & Posture (Jan. 2011) pp. 6-13, vol. 33.

Kuniyoshi, Y. et al., "Early motor development from partially ordered neural-body dynamics: experiments with a cortico-spinal-musculo-skeletal model" Biol Cybern (Nov. 2006) pp. 589-605, vol. 95.

Yamada, Y. et al., "Embodiment guides motor and spinal circuit development in vertebrate embryo and fetus" 2012 IEEE International Conference on Development and Learning and Epigenetic Robotics (ICDL) (Nov. 2012) pp. 1-6.

Ting, L.H. et al., "Neuromechanical Principles Underlying Movement Modularity and Their Implications for Rehabilitation" Neuron (Apr. 2015) pp. 38-54, vol. 86.

Cheung, V. et al., "Muscle synergy patterns as physiological markers of motor cortical damage" PNAS (Sep. 2012) pp. 1-9, vol. 109, No. 36.

Maughan, R.J. et al., "Strength and cross-sectional area of human skeletal muscle" J Physiol. (May 1983) pp. 37-49, vol. 338.

Yamada, Y. et al., "An Embodied Brain Model of the Human Foetus" Scientific Report (Jun. 2016) pp. 1-10, vol. 6.

Lee, S.H., "Biomechanical Modeling and Control of the Human Body for Computer Animation" A dissertation submitted in partial satisfaction of the requirements for the degree Doctor of Philosophy in Computer Science at the University of California (2008) pp. 1-143.

Shivashankar Reddy, A., "Musculoskeletal Biomechanics Simulation and Emg Analysis of Shoulder Muscles for Archery Sport" A Thesis Submitted to the College of Graduate Studies Texas A&M University—Kingsville, in partial fulfillment of the requirements for the degree of Master of Science (Dec. 2015) pp. 1-15.

* cited by examiner

ESTIMATION OF MUSCLE ACTIVITIES USING THE MUSCLES RELATIONSHIP DURING SIMULATING MOVEMENTS

BACKGROUND

Technical Field

The present invention relates to estimation of activity of muscles.

Related Art

Conventionally, in the fields of medical treatment and sports, muscle and skeletal structures are modeled, and the amount of muscle activity is estimated from motion data.

SUMMARY

According to one aspect of the present invention, provided is a computer implemented method comprising acquiring, for each of two or more muscles included in a musculoskeletal body model, a set of time-series data of muscle state change that accompanies motion of a body; calculating a correlation between the sets of time-series data for a pair of muscles included among the two or more muscles; and estimating activity of a plurality of muscles included in the musculoskeletal body model in a motion state that is an estimation target, using an objective function including a constraint using the correlation of the sets of time-series data.

According to another aspect of the present invention, provided is an apparatus comprising an acquisition section that, for each of two or more muscles included in a musculoskeletal body model, acquires a set of time-series data of muscle state change that accompanies motion of a body; a calculation section that calculates a correlation between the sets of time-series data for a pair of muscles included among the two or more muscles; and an estimation section that estimates activity of a plurality of muscles included in the musculoskeletal body model in a motion state that is an estimation target, using an objective function including a constraint using the correlation of the sets of time-series data.

According to still another aspect of the present invention, provided is a computer program product for estimating activity of a plurality of muscles included in a musculoskeletal body model, the computer program product comprising a computer readable storage medium having program instructions embodied therewith, the program instructions executable by a device to cause the device to perform operations comprising acquiring, for each of two or more muscles included in the musculoskeletal body model, a set of time-series data of muscle state change that accompanies motion of a body; calculating a correlation between the sets of time-series data for a pair of muscles included among the two or more muscles; and estimating activity of a plurality of muscles included in the musculoskeletal body model in a motion state that is an estimation target, using an objective function including a constraint using the correlation of the sets of time-series data.

The summary clause does not necessarily describe all necessary features of the embodiments of the present invention. The present invention may also be a sub-combination of the features described above. The above and other features and advantages of the present invention will become more apparent from the following description of the embodiments taken in conjunction with the accompanying drawings.

DESCRIPTION OF EXEMPLARY EMBODIMENTS

Hereinafter, (some) embodiment(s) of the present invention will be described. The embodiment(s) do(es) not limit the invention according to the claims, and all the combinations of the features described in the embodiment(s) are not necessarily essential to means provided by aspects of the invention.

Figure 1:
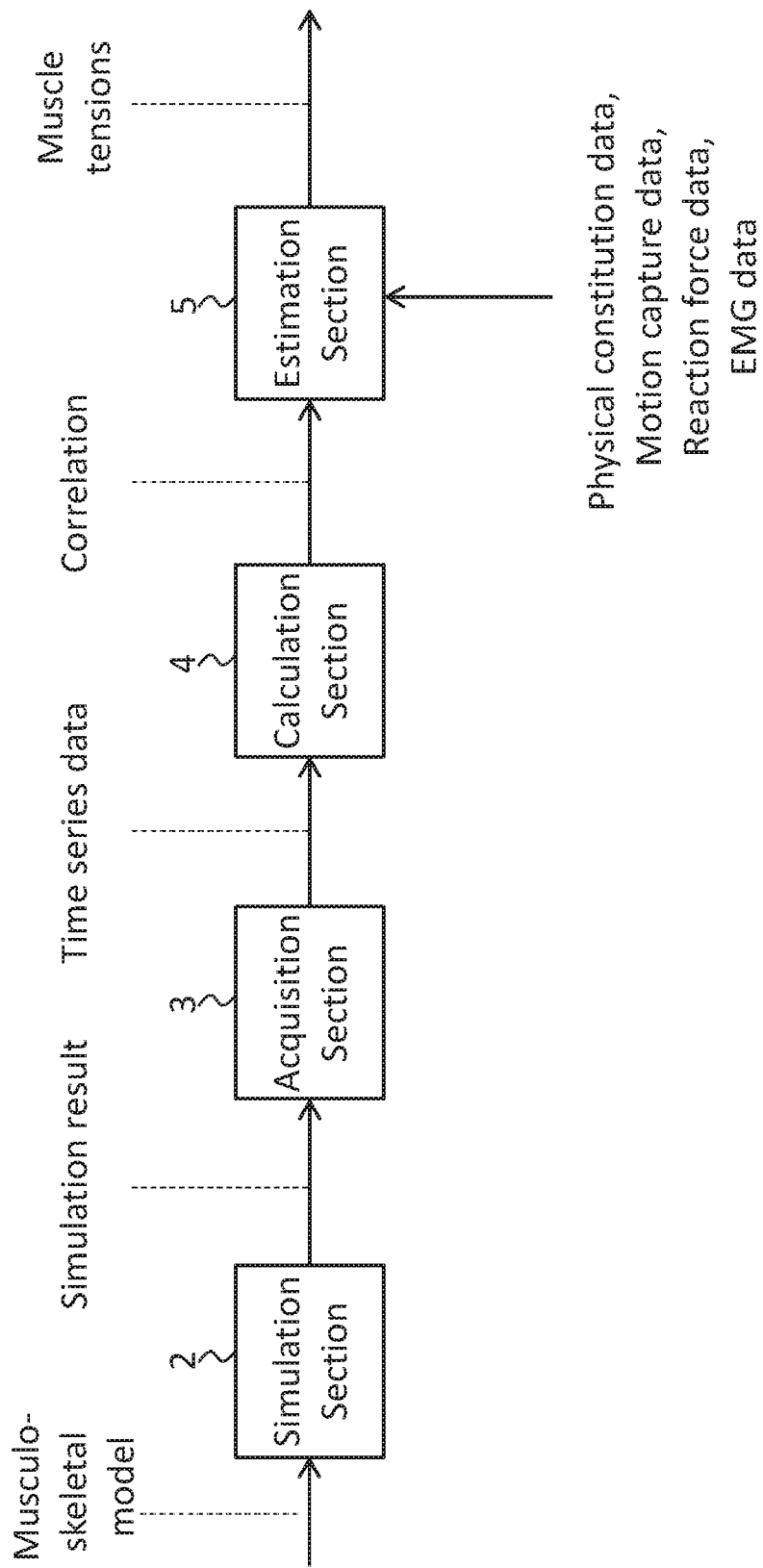
FIG. 1 shows an apparatus 1 according to an embodiment of the present invention.

FIG. 1 shows an apparatus 1 according to an embodiment of the present invention. The apparatus 1 estimates the activity of a plurality of muscles contained in a living creature. As one example of the present embodiment, the apparatus 1 estimates values corresponding to muscle tensions of a plurality of muscles contained in a human body, e.g., the body of a test subject. Here, a value corresponding to muscle tension is the muscle tension itself, as an example in the present embodiment, but may instead be a value obtained by adding a constant value to the muscle tension or by multiplying the muscle tension by a constant value. The apparatus 1 includes a simulation section 2, an acquisition section 3, a calculation section 4, and an estimation section 5.

The simulation section 2 performs a motion simulation in which a model of a body represented as a musculoskeletal body model moves. The musculoskeletal body model is a model in which muscles are attached as contracting actuators to a skeletal body model having a linked structure in which bones of a human body are connected to each other by joints. The simulation section 2 may perform the simulation using a neural network model such as a spinal circuit model including neural oscillators, motion capture data of a test subject, the angles of a plurality of joints that realize a desired motion state, and the like. The techniques recorded in Documents (i) to (iii) below can be used as the techniques for performing such a simulation.

(i) Yamada, Y. et al. An Embodied Brain Model of the Human Foetus. Sci. Rep. 6, 27893; doi: 10.1038/srep27893 (2016).

(ii) Yamada, Y. & Kuniyoshi, Y. Embodiment guides motor and spinal circuit development in vertebrate embryo and fetus. IEEE Int. Conf. Dev. Learn. 1-6 (2012).

(iii) Kuniyoshi Y, Sangawa S. Early motor development from partially ordered neural-body dynamics: experiments with a cortico-spinal-musculo-skeletal body model. Biol. Cybern. 95, 589-605 (2006).

The simulation section 2 may simulate, for one or more muscles, a change in the muscle state that accompanies motion in the motion simulation. The change in the muscle state may include at least one of change in muscle length, change in muscle tension, change in the output of motor neurons for a muscle, change in the output of a spinal circuit model, and data obtained by capturing the motion of a person. The simulation section 2 may supply the simulation results to the acquisition section 3.

The acquisition section 3 acquires time-series data of the muscle state change that accompanies motion of the body, for each of two or more muscles included in the musculoskeletal body model. The two or more muscles included in the musculoskeletal body model may be some of the muscles included in the musculoskeletal body model, or may be all of the muscles included in the musculoskeletal body model.

The acquisition section 3 may acquire the time-series data of the muscle state change from the simulation section 2, and may also acquire time-series data from a sensor attached to the body of the test subject, e.g., a position sensor, acceleration sensor, or the like. The acquisition section 3 may supply the calculation section 4 with the acquired time-series data.

The calculation section 4 calculates the correlation between respective sets of time-series data of a pair of muscles, e.g., each pair in the present embodiment, among the two or more muscles for which the time-series data was acquired. The calculation section 4 may supply the estimation section 5 with the calculated correlation.

The estimation section 5 estimates the muscle tension of a plurality of muscles included in the musculoskeletal body model. The plurality of muscles for which the estimation is performed may be some or all of the muscles included in the musculoskeletal body model, or may be some or all of the two or more muscles for which the time-series data was acquired.

In a musculoskeletal body model including a large number of muscles, there is a redundancy problem that muscle tension is not uniquely determined from the motion data, and therefore the estimation section 5 sets an objective function (evaluation function) and calculates the muscle tension by optimizing this objective function. For example, the estimation section 5 may estimate the muscle tensions of the plurality of muscles in a motion state that is the estimation target, by using the objective function including a constraint using the correlation calculated by the calculation section 4. As an example, the estimation section 5 may determine the objective function including the muscle tension of each of the plurality of muscles, and estimate each muscle tension at the time when the value of this objective function is at a maximum or minimum to be the muscle tension of this muscle.

Furthermore, the estimation section 5 may determine the objective function to be a function including a constraint using joint torques of a plurality of joints. In this way, it is possible to estimate muscle tension such that the muscle tension spreads to each muscle by the joint torque via the muscle pathways of the muscles in the musculoskeletal body model. The plurality of joints included in the musculoskeletal body model may be some or all of the joints included in the musculoskeletal body model. The estimation section 5 may estimate the joint torques using physical constitution data of the test subject, motion capture data of the test subject, measured data of the reactive force, and the like, to determine the objective function.

Furthermore, the estimation section 5 may determine the objective function to be a function including a constraint using one or more of the muscle tensions based on measured data. In this way, it is possible to estimate muscle tension that approximates the actual muscle tension. The estimation section 5 may calculate the muscle tensions based on measured data obtained using electromyography data or the like, to determine the objective function. The estimation section 5 may output the estimated muscle tensions to the outside of the apparatus 1.

With the apparatus 1 described above, the correlation of the time-series data of the muscle state change among a plurality of muscles included in the musculoskeletal body model is calculated, and therefore it is possible to accurately detect the correlation relationship among the plurality of muscles. Furthermore, the tensions of the plurality of muscles are estimated using the objective function including the constraint using this correlation, and therefore it is possible to improve the estimation accuracy compared to a case in which the tensions are estimated using an objective function that includes constraint conditions based on experience. Yet further, there is no need for the time and effort of determining constraint conditions.

Since the correlation between sets of time-series data for each pair of muscles included in the plurality of muscles is calculated, it is possible to more accurately detect the correlation relationship among the plurality of muscles, compared to a case where the correlation between sets of time-series data for only some pairs of muscles is calculated.

Furthermore, since the time-series data of the muscle state change is acquired using a motion simulation, it is possible to simplify the acquisition of the time-series data, compared to a case where measurement is performed using a sensor. Yet further, the time-series data can also be used in a case where measurement is not performed using a sensor.

Figure 2:
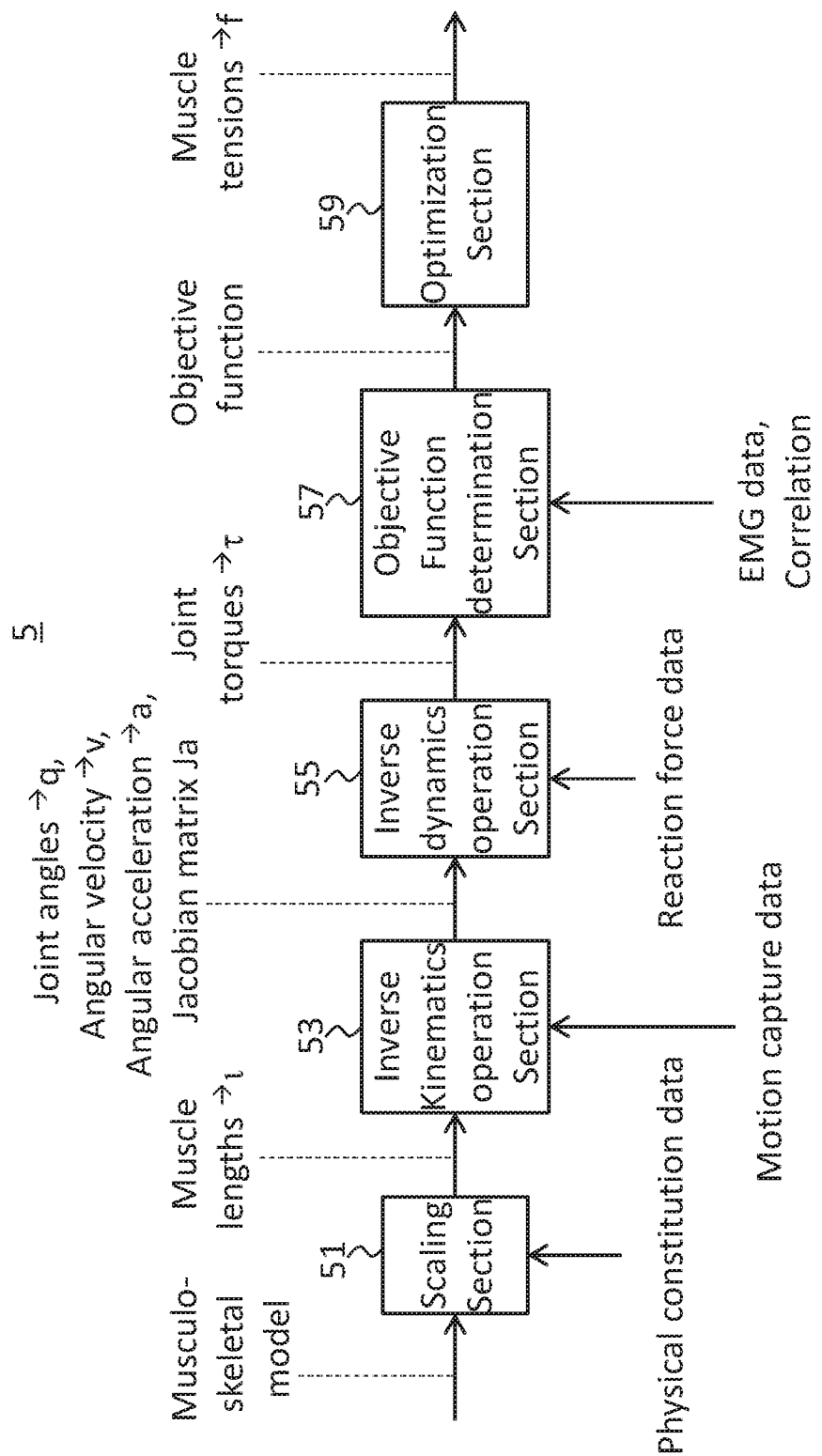
FIG. 2 shows an estimation section of the apparatus.

FIG. 2 shows the estimation section 5. The estimation section 5 includes a scaling section 51, an inverse kinematics operation section 53, an inverse dynamics operation section 55, an objective function determination section 57, and an optimization section 59.

The scaling section 51 performs scaling of the musculoskeletal body model. For example, the scaling section 51 may perform scaling of a standard musculoskeletal body model stored therein, in accordance with the body of the test subject. As an example, the scaling section 51 may perform scaling based on measured data of physical constitution of the test subject. As a result of the scaling, the length ($\vec{\iota}$) of each muscle among I muscles (where I is a natural number greater than or equal to 2) that are targets of the muscle tension estimation may be calculated. Here, "$\vec{\iota}$" indicates the vector $\iota$. The scaling section 51 may store a plurality of standard musculoskeletal body models, and may perform scaling by selecting one of these musculoskeletal body models according to a manipulation by an operator. The scaling section 51 may supply the inverse kinematics operation section 53 with the I muscle lengths ($\vec{\iota}$).

The inverse kinematics operation section 53 calculates the joint angles, angular velocities and angular accelerations of a plurality of joints in a motion state that is the estimation target. For example, the inverse kinematics operation section 53 may match a musculoskeletal body model to the motion state that is the estimation target, extract the joint angles of the plurality of joints from the matched musculoskeletal body model, and calculate angular velocities and angular accelerations of the plurality of joints based on the time-series data of the joint angles. As an example, the inverse kinematics operation section 53 may alter the shape of the musculoskeletal body model to realize the motion state that is the estimation target. Furthermore, the inverse kinematics operation section 53 may perform an inverse kinematics operation to obtain the joint angles of the plurality of joints from the position and motion state of one or more end points (e.g., finger tips) of the musculoskeletal body model. Yet further, the inverse kinematics operation section 53 may calculate the joint angles based on the motion capture data of the motion state that is the estimation target. The inverse kinematics operation section 53 may calculate the joint angles ($\vec{q}$), angular velocities ($\vec{v}$) and angular accelerations ($\vec{a}$) of J joints (where J is a natural number greater than or equal to 2) connected to the I muscles that are targets of the muscle tension estimation.

The inverse kinematics operation section 53 may calculate the Jacob matrix (Ja) of the length ($\iota$) of each muscle for the joint angle (q) of each joint in the motion state that is the estimation target. For example, the inverse kinematics operation section 53 may generate a Jacob matrix (Ja) with I rows and J columns by calculating, for each value of (i, j), the rate of change of the length ($\iota_i$) of the i-th muscle (where i is a natural number and $1 \leq i \leq I$) for the joint angle ($q_j$) of the j-th joint (where j is a natural number and $1 \leq j \leq J$). The computational content of the inverse kinematics operation section 53 may be the computational content disclosed in Japanese Patent Application Publication No. 2010-29340 and U.S. Pat. No. 7,308,826. The inverse kinematics operation section 53 may supply the inverse dynamics operation section 55 with the obtained joint angles ($\vec{q}$), angular velocities ($\vec{v}$), angular accelerations ($\vec{a}$) and Jacob matrix (Ja).

The inverse dynamics operation section 55 estimates the joint torques of a plurality of joints, based on the joint angles ($\vec{q}$), angular velocities ($\vec{v}$) and angular accelerations ($\vec{a}$) of a plurality of joints of the musculoskeletal body model in the motion state that is the estimation target. For example, the inverse dynamics operation section 55 may perform an inverse dynamics operation using measured data of the reactive force applied to the test subject from the floor or the like, to calculate the joint torque that is optimal for realizing the motion state that is the estimation target, in which the plurality of joints have the joint angles ($\vec{q}$), angular velocities ($\vec{v}$) and angular accelerations ($\vec{a}$). The inverse dynamics operation section 55 may calculate the joint torques ($\vec{\tau}$) of the J joints described above. Among the joint torques ($\vec{\tau}$) of the J joints, the values of joint torques ($\tau_j$) that cannot be calculated may be set to 0. The computational content of the inverse dynamics operation section 55 may be the computational content disclosed in Japanese Patent Application Publication No. 2010-29340 and U.S. Pat. No. 7,308,826. The inverse dynamics operation section 55 may supply the objective function determination section 57 with the calculated torques ($\vec{\tau}$).

The objective function determination section 57 determines the objective function that includes the muscle tensions ($\vec{f}$) of the I muscles and the joint torques ($\vec{\tau}$) of the J joints. As an example in the present embodiment, the objective function is the function inside the brackets in Expression 1. This objective function is used to calculate the muscle tension ($\vec{f}$) that minimizes the value of the objective function.

$$\vec{f} = \arg\min_{\vec{f}} \left[ \vec{\delta}_\tau^T a_\tau^T \vec{\delta}_\tau + \vec{\delta}_f^T a_f^T \vec{\delta}_f + \vec{\delta}_c^T a_c^T \vec{\delta}_c \right] \quad \text{Expression 1}$$

Here, the first term in the objective function is a squared error term for the joint torque of each joint. As shown in Expression 2, for example, $\vec{\delta}_\tau$ in the first term is the estimation error of the joint torques ($\vec{\tau}$) of the J joints, and indicates the difference between the joint torques ($\vec{\tau}$) calculated by the inverse dynamics operation section 55 based on the measured data and the estimated joint torques ($Ja^T \cdot \vec{f}$) using the estimated muscle tensions ($\vec{f}$) of the I muscles. As an example in the present embodiment, the first term is weighted with a weight ($a^\tau$). The weight ($a_\tau$) may be a matrix that includes J×J values set arbitrarily for each pair of joints, using cross validation, or may be a single scalar value. The first term does not need to include the weight ($a_\tau$). The first term described above may be the term disclosed in Japanese Patent Application Publication No. 2010-29340 and U.S. Pat. No. 7,308,826.

$$\vec{\delta}_\tau = \vec{\tau} - Ja^T \vec{f} \quad \text{Expression 2}$$

The second term of the objective function is a squared error term for the muscle tension of each muscle. As shown in Expression 3, for example, $\vec{\delta}_f$ in the second term is the estimation error of the muscle tensions ($\vec{f}$) of the I muscles, and indicates the difference between the estimated muscle tensions ($\vec{f}$) and the muscle tensions ($\vec{f}*$) calculated from the measured data of the electromyograph. Among the muscle tensions ($\vec{f}*$) of the I muscles, values of muscle tensions ($f_i*$) that cannot be calculated may be set to 0. Since the estimated muscle tensions ($\vec{f}$) are tensile forces, these muscle tensions are negative values in the example of the present embodiment. Furthermore, as an example in the present embodiment, the second term is weighted with a weight ($a_f$). The weight ($a_f$) may be a matrix that includes I×I values set arbitrarily for each pair of muscles, using cross validation, or may be a single scalar value. The second term does not need to include the weight ($a_f$). The second term and the technique for calculating the muscle tensions from the measured data of the electromyograph described above may be the term and technique disclosed in Japanese Patent Application Publication No. 2010-29340 and U.S. Pat. No. 7,308,826.

$$\vec{\delta}_f = \vec{f} - \vec{f}*, \ f \leq 0 \quad \text{Expression 3}$$

The third term of the objective function is a term relating to the constraint using the correlation calculated by the calculation section 4. For example, as shown in Expression 4, $\vec{\delta}_c$ in the third term may be the product of the Laplacian matrix ($E_c$) calculated as the correlation by the calculation section 4 and the estimated muscle tensions ($\vec{f}$). As a result of such a third term, the quadratic sum of all the elements in the vector $\vec{\delta}_c$ is included in the objective function as an error term. As an example in the present embodiment, the third term is weighted with a weight ($a_c$). The weight ($a_c$) may be a matrix that includes I×I values set arbitrarily for each pair of muscles, using cross validation, or may be a single scalar value. The third term does not need to include the weight ($a_f$).

$$\vec{\delta}_c = E_c \vec{f} \quad \text{Expression 4}$$

Here, the Laplacian matrix ($E_c$) may include a row and a column corresponding to each muscle and, as an example in the present embodiment, may be a square matrix with I rows and I columns corresponding to the I muscles. Each off-diagonal element in the Laplacian matrix may be the additive inverse of a correlation value between the muscle corresponding to the row and the muscle corresponding to the column. Each on-diagonal element in the Laplacian matrix may be the correlation value corresponding to the off-diagonal element of each column, or may be the total sum of the correlation values corresponding to the off-diagonal vales of each row. For example, the Laplacian matrix may be the matrix $E_c$ shown in Expression 5 using the adjacency matrix (A) and the degree matrix (D) with I columns and I rows.

$$E_C = D - A \quad \text{Expression 5}$$

Here, the on-diagonal elements in the adjacency matrix (A) are 0, and the off-diagonal elements are the correlation values between the muscle corresponding to the row and the muscle corresponding to the column. For example, the element $A_{mn}$ at row m and column n (where m and n are natural numbers, $1 \le m \le I$, and $1 \le n \le I$) of the adjacency matrix (A) may be the value shown in Expression 6. In this expression, $f(x_m, x_n)$ is the Pearson correlation between the time-series data of the m-th muscle and the time-series data of the n-th muscle. Furthermore, $f(x_m, x_n)$ exhibits the value as-is if the value of the Pearson correlation is greater than or equal to 0, and exhibits a value of 0 if the value of the Pearson correlation is negative. As a result, the correlation value is 0 if the sets of time-series data have a negative correlation.

$$A_{mn} = \begin{cases} 0, & m = n \\ (f(x_m, x_n))_+, & m \ne n \end{cases} \quad \text{Expression 6}$$

The off-diagonal elements of the degree matrix (D) are 0, and the on-diagonal elements are the total sums of the correlation values between muscles corresponding to the row associated with this element and each muscle corresponding to each column. As an example, the element $D_{mn}$ in row m and column n of the degree matrix D may be the value shown in Expression 7.

$$D_{mn} = \begin{cases} \sum_n A_{mn}, & m = n \\ 0, & m \ne n \end{cases} \quad \text{Expression 7}$$

The objective function determination section 57 may supply the optimization section 59 with the determined objective function.

The optimization section 59 calculates the muscle tensions ($\vec{f}$) at the time when the value of the objective function is at a minimum. The technique for calculating the muscle tensions ($\vec{f}$) may be the technique disclosed in Japanese Patent Application Publication No. 2010-29340 and U.S. Pat. No. 7,308,826.

With the estimation section 5 described above, the quadratic sum or weighted quadratic sum of all the elements in the vector obtained as the product of the Laplacian matrix ($E_c$) indicating the correlations between muscles and the muscle tensions ($\vec{f}$) of the plurality of muscles is included in the objective function as an error term, and therefore it is possible to improve the estimation accuracy of the muscle tension.

Figure 3:
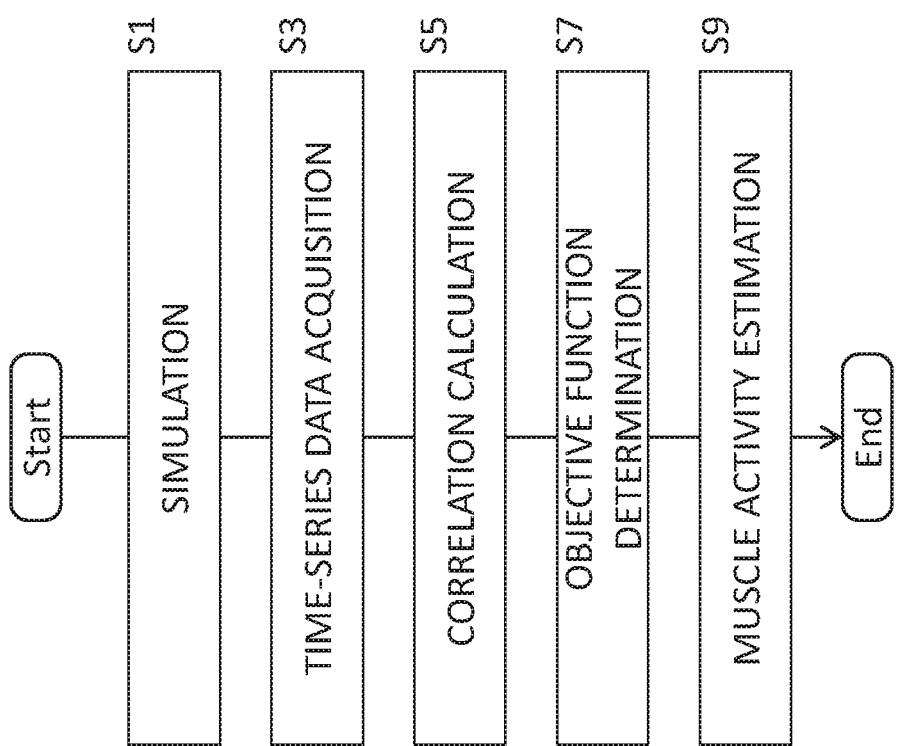
FIG. 3 shows a method performed by the apparatus.

FIG. 3 shows a method performed by the apparatus 1. The apparatus 1 estimates the muscle tensions ($\vec{f}$) using steps S1 to S9.

First, at step S1, the simulation section 2 performs the motion simulation. The simulation section 2 may perform the simulation using the musculoskeletal body model scaled by the scaling section 51. In the simulation, the simulation section 2 may move the model of the body represented by the musculoskeletal body model with each of a plurality of types of motion patterns. The plurality of types of motion patterns are, for example, a motion pattern of bending a knee, a motion pattern of advancing a knee, a motion pattern of walking, and the like.

Next, at step S3, the acquisition section 3 acquires the time-series data of the muscle change state that accompanies the motion of the body, for each of the two or more muscles. The acquisition section 3 may acquire time-series data of a sensor attached to the body of the test subject, in addition to the time-series data from the simulation section 2. If the time-series data is acquired from the simulation section 2, the acquisition section 3 may select a motion pattern relating to the motion state that is the estimation target from among the plurality of types of motion patterns that can be simulated by the simulation section 2, and acquire the time-series data for the selected motion pattern. Instead of this, the acquisition section 3 may acquire the time-series data of a random motion pattern that is unrelated to the motion state that is the estimation target. The time window for acquiring the time-series data may be set arbitrarily and if, for example, the motion that is the estimation target is periodic motion and the period of this motion is, e.g., two seconds, may be set to have a length greater than or equal to two seconds.

Next, at step S5, the calculation section 4 calculates the correlation between the sets of time-series data for each pair of muscles included among the two or more muscles. For example, the calculation section 4 may calculate the Laplacian matrix ($E_c$) described above as the correlation.

Next, at step S7, the objective function determination section 57 determines the objective function that includes a constraint using the correlation between the sets of time-series data. For example, the estimation section 5 may determine the objective function shown in Expression 1 above. If the joint torques ($\vec{\tau}$) are necessary to determine the objective function, the inverse kinematics operation section 53 may match the musculoskeletal body model in the motion state that is the estimation target and extract the joint angles ($\vec{q}$) of the plurality of joints from the matched musculoskeletal body model. Furthermore, the inverse dynamics operation section 55 may estimate the joint torques ($\vec{\tau}$) based on the joint angles ($\vec{q}$) in the motion state that is the estimation target.

Next, at step S9, the optimization section 59 estimates the muscle tensions ($\vec{f}$) of the I muscles using the objective function.

With the method described above, the musculoskeletal body model is matched to the motion state that is the estimation target and the muscle tensions ($\vec{f}$) are estimated by estimating the joint angles ($\vec{q}$) and the joint torques ($\vec{\tau}$) of the plurality of joints from the matched musculoskeletal body model, and therefore it is possible to further improve the estimation accuracy compared to a case where the estimation is performed without matching the musculoskeletal body model.

Furthermore, the motion pattern relating to the motion state that is the estimation target is selected from among the plurality of types of motion patterns and the time-series data is acquired for the selected motion pattern, and therefore it is possible to accurately calculate the correlation in the motion state that is the estimation target. Accordingly, it is possible to further improve the estimation accuracy.

In the embodiment described above, the apparatus 1 is described as acquiring the time-series data of the muscle state change from the simulation section 2, but the time-series data may instead be acquired from only a sensor attached to the body of the test subject. In this case, the apparatus 1 does not need to include the simulation section 2.

Furthermore, in the above description, the Laplacian matrix ($E_c$) includes the total values of the correlation values corresponding to the off-diagonal elements of each row or each column in the on-diagonal elements, and includes a negative value as the correlation value between the muscle corresponding to the row and the muscle corresponding to the column in each off-diagonal element. However, the Laplacian matrix ($E_c$) may include the total values of the absolute values of the correlation values corresponding to the off-diagonal elements of each row or each column in the on-diagonal elements, and include a negative value as the correlation value between the muscle corresponding to the row and the muscle corresponding to the column in each off-diagonal element. For example, a correlation value that is less than 0 may be included in the off-diagonal elements of the adjacency matrix (A) used to calculate the Laplacian matrix in Expression 5. As one example, each element $A_{mn}$ of the adjacency matrix (A) may be the value shown in Expression 6'. Furthermore, each element $D_{mn}$ of the degree matrix may be the value shown in Expression 7'.

$$A_{mn} = \begin{cases} 0, m = n \\ f(x_m, x_n), m \neq n \end{cases} \quad \text{Expression 6'}$$

$$D_{mn} = \begin{cases} \sum_n |A_{mn}|, m = n \\ 0, m \neq n \end{cases} \quad \text{Expression 7'}$$

Furthermore, the objective function is described as including a first term that is the square error term for the joint torque and a second term that is a square error term for the muscle tension of each muscle, but at least one of these terms may be omitted and/or one or more of other terms may be included in the objective function. For example, the objective function may include a square error term represented by $\vec{\delta}_m{}^T a_m{}^T \vec{\delta}_m$ as the constraint condition set through experience. As shown in Expression 8, $\vec{\delta}_m$ may be the product of a Laplacian matrix ($E_G$) and the estimated muscle tensions ($\vec{f}$). The Laplacian matrix ($E_G$) includes rows and columns corresponding respectively to the muscles, and each value may be set to indicate the correlation between muscles, through cross validation. As an example, each value of the Laplacian matrix ($E_G$) may be set according to whether the value is associated with a muscle group in which the muscles have the same movement as each other and whether the muscles correspond physiologically. Such a square error term may be the term disclosed in Japanese Patent Application Publication No. 2010-29340 and U.S. Pat. No. 7,308,826.

$$\vec{\delta}_m = E_G \vec{f} \quad \text{Expression 8}$$

Furthermore, the apparatus 1 is described as estimating values corresponding to a plurality of muscle tensions as the activity of the plurality of muscles, but instead of or in addition to this, the apparatus 1 may estimate values corresponding to at least one of the ratios of the muscle tensions to the largest muscle tension, the cross-sectional areas of the muscles, and the ratios of the cross-sectional areas of the muscles to the maximum cross-sectional area of a muscle. The muscle tension relative to the maximum muscle tension is the muscle strength relative to the maximum voluntary contraction force and, when estimating this ratios ($\vec{r}$), the objective function determination section 57 may determine the objective function shown in Expression 1'. Each element (r) among the ratios ($\vec{r}$) may be such that $0 \leq r \leq 1$. For example, as shown in Document (iv) below, the maximum muscle tension may be estimated using the cross-sectional muscle area obtained from MRI/CT data, or may be measured.

Document (iv): Maughan R, Watson J, Weir J. Strength and cross-sectional area of human skeletal muscle. J. Physiol. 338, 37-49 (1983).

$$\vec{r} = \arg\min_{\vec{r}} \left[ \vec{\delta}_\tau{}^T a_\tau{}^T \vec{\delta}_\tau + \vec{\delta}_f{}^T a_f{}^T \vec{\delta}_f + \vec{\delta}_c{}^T a_c{}^T \vec{\delta}_c \right] \quad \text{Expression 1'}$$

Here, as shown in Expression 2', $\vec{\delta}_\tau$ indicates the difference between the joint torques ($\vec{\tau}$) calculated by the inverse dynamics operation section 55 based on the measured data and the estimated torques ($Ja^T \cdot F \cdot \vec{r}$) using the estimated ratios ($\vec{r}$) of the I muscles. Here, F is a square matrix with I rows and I columns wherein, as shown in Expression 9, the off-diagonal elements are 0 and the on-diagonal elements are the maximum muscle tensions of the muscles corresponding to the row and column. As shown in Expression 3', $\vec{\delta}_f$ indicates the difference between the estimated ratios ($\vec{r}$) and the ratios ($\vec{r}^*$) calculated from the measured data of the electromyograph. Among the ratios ($\vec{r}$) of the I muscles, the value of ratios ($r_i^*$) that cannot be calculated may be set to be 0. As shown in Expression 4', $\vec{\delta}_c$ may be the product of the Laplacian matrix ($E_c$) calculated as the correlation and the estimated ratios ($\vec{r}$). Instead, as shown in Expression 4'', $\vec{\delta}_c$ may be the product of the Laplacian matrix ($E_c$) calculated as the correlation and the standard deviation ($2\times(\vec{r}-0.5)$) of the estimated ratios ($\vec{r}$). As an example in the present embodiment, each term in the objective function may by weighted with a weight (a). Each weight (a) may be a matrix including I×I values set arbitrarily, through cross validation, for each pair of muscles, may be a matrix including J×J values set arbitrarily, through cross validation, for each pair of joints, or may be a single scalar value. Each term does not need to include a weight (a). The objective function may omit at least one of the first term and the second term, and include the other. For example, the objective function may include another square error term represented by $\vec{\delta}_m{}^T a_m{}^T \vec{\delta}_m$ as the constraint condition set through experience, and $\vec{\delta}_m$ may be the product of a Laplacian matrix ($E_G$) and the estimated ratios ($\vec{r}$), as shown in Expression 8'.

$$\vec{\delta}_\tau = \vec{\tau} - Ja^T F \vec{r} \quad \text{Expression 2'}$$

$$F_{mn} = \begin{cases} F_{m,max}, m = n \\ 0, m \neq n \end{cases} \quad \text{Expression 9}$$

$$\vec{\delta}_f = \vec{r} - \vec{r}^* \quad \text{Expression 3'}$$

$$\vec{\delta}_c = E_c \vec{r} \quad \text{Expression 4'}$$

$$\vec{\delta}_c = E_c \{2 * (\vec{r} - 0.5)\} \quad \text{Expression 4''}$$

$$\vec{\delta}_m = E_G \vec{r} \quad \text{Expression 8'}$$

Figure 4:
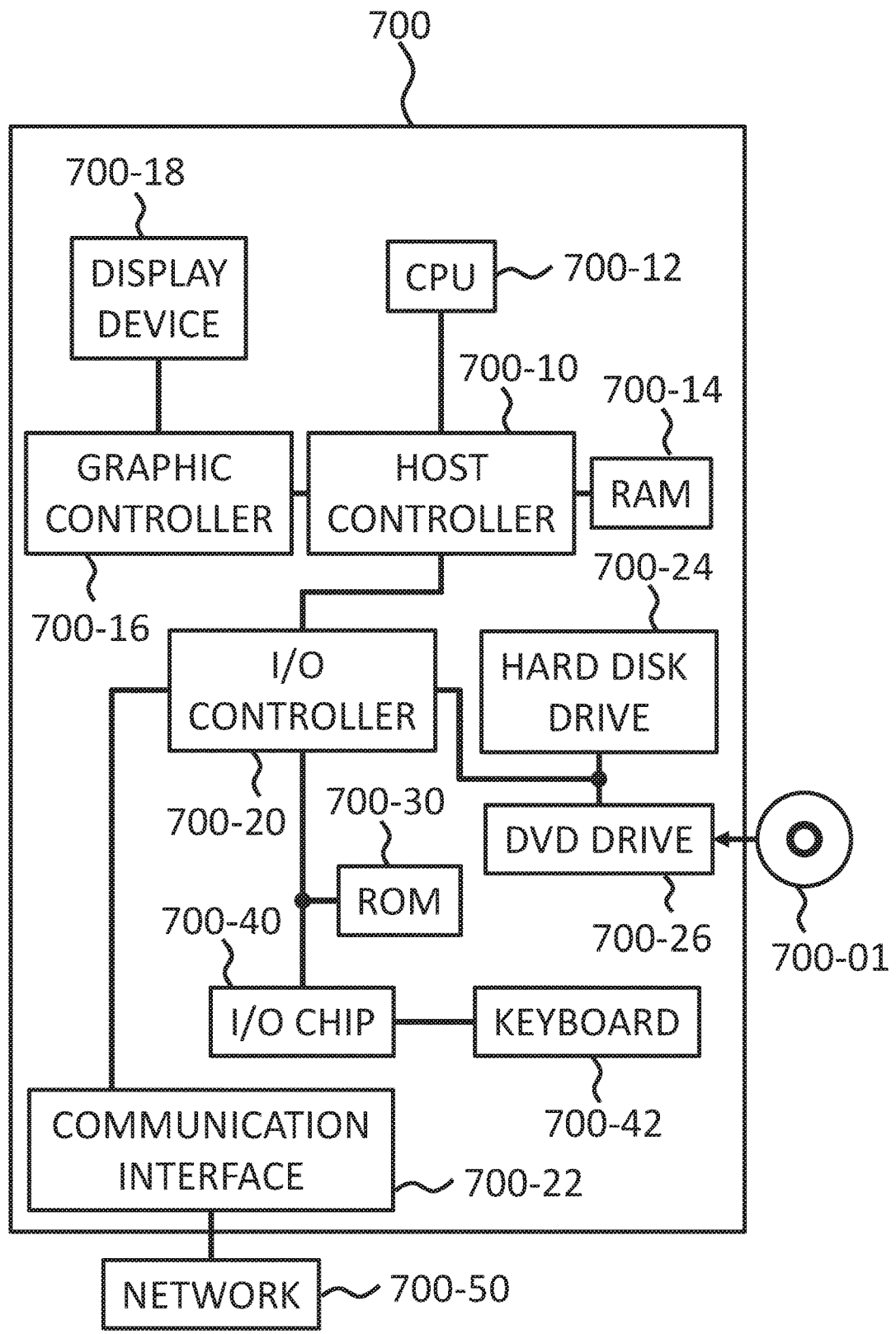
FIG. 4 shows an exemplary hardware configuration of a computer according to the embodiment of the invention.

FIG. 4 shows an exemplary hardware configuration of a computer configured to perform the foregoing operations, according to an embodiment of the present invention. A program that is installed in the computer 700 can cause the computer 700 to function as or perform operations associated with apparatuses of the embodiments of the present invention or one or more sections (including modules, components, elements, etc.) thereof, and/or cause the computer 700 to perform processes of the embodiments of the present invention or steps thereof. Such a program may be executed by the CPU 700-12 to cause the computer 700 to perform certain operations associated with some or all of the blocks of flowcharts and block diagrams described herein.

The computer 700 according to the present embodiment includes a CPU 700-12, a RAM 700-14, a graphics controller 700-16, and a display device 700-18, which are mutually connected by a host controller 700-10. The computer 700 also includes input/output units such as a communication interface 700-22, a hard disk drive 700-24, a DVD-ROM drive 700-26 and an IC card drive, which are connected to the host controller 700-10 via an input/output controller 700-20. The computer also includes legacy input/output units such as a ROM 700-30 and a keyboard 700-42, which are connected to the input/output controller 700-20 through an input/output chip 700-40.

The CPU 700-12 operates according to programs stored in the ROM 700-30 and the RAM 700-14, thereby controlling each unit. The graphics controller 700-16 obtains image data generated by the CPU 700-12 on a frame buffer or the like provided in the RAM 700-14 or in itself, and causes the image data to be displayed on the display device 700-18.

The communication interface 700-22 communicates with other electronic devices via a network 700-50. The hard disk drive 700-24 stores programs and data used by the CPU 700-12 within the computer 700. The DVD-ROM drive 700-26 reads the programs or the data from the DVD-ROM 700-01, and provides the hard disk drive 700-24 with the programs or the data via the RAM 700-14. The IC card drive reads programs and data from an IC card, and/or writes programs and data into the IC card.

The ROM 700-30 stores therein a boot program or the like executed by the computer 700 at the time of activation, and/or a program depending on the hardware of the computer 700. The input/output chip 700-40 may also connect various input/output units via a parallel port, a serial port, a keyboard port, a mouse port, and the like to the input/output controller 700-20.

A program is provided by computer readable media such as the DVD-ROM 700-01 or the IC card. The program is read from the computer readable media, installed into the hard disk drive 700-24, RAM 700-14, or ROM 700-30, which are also examples of computer readable media, and executed by the CPU 700-12. The information processing described in these programs is read into the computer 700, resulting in cooperation between a program and the above-mentioned various types of hardware resources. An apparatus or method may be constituted by realizing the operation or processing of information in accordance with the usage of the computer 700-

For example, when communication is performed between the computer 700 and an external device, the CPU 700-12 may execute a communication program loaded onto the RAM 700-14 to instruct communication processing to the communication interface 700-22, based on the processing described in the communication program. The communication interface 700-22, under control of the CPU 700-12, reads transmission data stored on a transmission buffering region provided in a recording medium such as the RAM 700-14, the hard disk drive 700-24, the DVD-ROM 700-01, or the IC card, and transmits the read transmission data to network 700-50 or writes reception data received from network 700-50 to a reception buffering region or the like provided on the recording medium.

In addition, the CPU 700-12 may cause all or a necessary portion of a file or a database to be read into the RAM 700-14, the file or the database having been stored in an external recording medium such as the hard disk drive 700-24, the DVD-ROM drive 700-26 (DVD-ROM 700-01), the IC card, etc., and perform various types of processing on the data on the RAM 700-14. The CPU 700-12 may then write back the processed data to the external recording medium.

Various types of information, such as various types of programs, data, tables, and databases, may be stored in the recording medium to undergo information processing. The CPU 700-12 may perform various types of processing on the data read from the RAM 700-14, which includes various types of operations, processing of information, condition judging, conditional branch, unconditional branch, search/replace of information, etc., as described throughout this disclosure and designated by an instruction sequence of programs, and writes the result back to the RAM 700-14. In addition, the CPU 700-12 may search for information in a file, a database, etc., in the recording medium. For example, when a plurality of entries, each having an attribute value of a first attribute is associated with an attribute value of a second attribute, are stored in the recording medium, the CPU 700-12 may search for an entry matching the condition whose attribute value of the first attribute is designated, from among the plurality of entries, and reads the attribute value of the second attribute stored in the entry, thereby obtaining the attribute value of the second attribute associated with the first attribute satisfying the predetermined condition.

The above-explained program or software modules may be stored in the computer readable media on or near the computer 700. In addition, a recording medium such as a hard disk or a RAM provided in a server system connected to a dedicated communication network or the Internet can be used as the computer readable media, thereby providing the program to the computer 700 via the network.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to individualize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

As made clear from the above description, with the embodiments of the present invention, it is possible to increase the estimation accuracy of muscle activity.

What is claimed is:

1. A computer implemented method comprising:
acquiring, for each of two or more muscles included in a musculoskeletal body model, a set of time-series data of muscle state change that accompanies motion of a body;
calculating, using a hardware processor, a correlation between the sets of time-series data for a pair of muscles included among the two or more muscles;
estimating joint torques using an inverse dynamics operation;
optimizing an objective function using the estimated joint torques; and estimating activity of a plurality of muscles included in the musculoskeletal body model in a motion state that is an estimation target using the optimized objective function including a constraint using the correlation of the sets of time-series data to improve estimation accuracy of the activity of the plurality of muscles included in the musculoskeletal body model.

2. The computer implemented method according to claim 1, further comprising:
performing a motion simulation in which a model of a body represented by the musculoskeletal body model moves, wherein
the acquiring includes acquiring time-series data of the muscle state change that accompanies the motion according to the motion simulation.

3. The computer implemented method according to claim 2, wherein
performing the motion simulation includes moving the model of the body represented by the musculoskeletal body model according to each of a plurality of types of motion patterns, and
the acquiring includes:
selecting a motion pattern relating to the motion state that is the estimation target from among the plurality of types of motion patterns; and
acquiring the time-series data for the motion pattern selected from among the plurality of types of motion patterns.

4. The computer implemented method according to claim 1, wherein
calculating the correlation includes calculating the correlation between the sets of time-series data for each pair of muscles included among the plurality of muscles.

5. The computer implemented method according to claim 4, wherein
calculating the correlation includes calculating a Laplacian matrix that has rows and columns corresponding to each muscle, includes additive inverses of correlation values between a muscle corresponding to a row and a muscle corresponding to a column in off-diagonal elements, and includes total values of correlation values corresponding to the off-diagonal elements of each row or each column in on-diagonal elements.

6. The computer implemented method according to claim 5, wherein
the error term of the objective function includes a quadratic sum or a weighted quadratic sum of all elements of a vector obtained as a product of activities of the plurality of muscles and the Laplacian matrix.

7. The computer implemented method according to claim 1, wherein
calculating the correlation includes setting a correlation value to 0 if there is a negative correlation between the sets of time-series data of the pair of muscles.

8. The computer implemented method according to claim 1, wherein
calculating the correlation includes calculating a Laplacian matrix that has rows and columns corresponding to each muscle, includes negative correlation values between a muscle corresponding to a row and a muscle corresponding to a column in off-diagonal elements, and includes absolute values of total values of correlation values corresponding to the off-diagonal elements of each row or each column in on-diagonal elements.

9. The computer implemented method according to claim 1, wherein calculating the correlation includes calculating a Pearson correlation between the sets of time-series data of the pair of muscles.

10. The computer implemented method according to claim 1, wherein
the muscle state change includes at least one of change in muscle length, change in muscle tension, change in output of motor neurons for the muscle, change in output of a spinal circuit model, and data obtained by capturing movement of a person.

11. The computer implemented method according to claim 1, wherein
the activity of each of the plurality of muscles is a value corresponding to at least one of muscle tension, a ratio of muscle tension to a maximum muscle tension, cross-sectional muscle area, and a ratio of the cross-sectional muscle area to a maximum cross-sectional muscle area.

12. The computer implemented method according to claim 1, wherein,
estimating the joint torques includes estimating joint torques of a plurality of joints based on joint angles, angular velocities and angular accelerations of the plurality of joints included in the musculoskeletal body model in a motion state that is an estimation target,
wherein the objective function includes a constraint using the joint torques.

13. The computer implemented method according to claim 12, further comprising:
matching the musculoskeletal body model to the motion state that is the estimation target; and
extracting the joint angles, the angular velocities and the angular accelerations of the plurality of joints from the musculoskeletal body model matched to the motion state that is the estimation target.

14. An apparatus comprising:
one or more processors;
an acquisition section operably connected to a processor of the one or more processors that, for each of two or more muscles included in a musculoskeletal body model, acquires a set of time-series data of muscle state change that accompanies motion of a body;
a calculation section operably connected to a processor of the one or more processors that calculates a correlation between the sets of time-series data for a pair of muscles included among the two or more muscles;
an inverse dynamics operation section operably connected to a processor of the one or more processor that estimates joint torques of a plurality of joints;
an objective function determination section operably connected to a processor of the one or more processors that optimizes an objective function using the estimated joint torques; and
an estimation section operably connected to a processor of the one or more processors that estimates activity of a plurality of muscles included in the musculoskeletal body model in a motion state that is an estimation target using the optimized objective function including a constraint using the correlation of the sets of time-series data to improve estimation accuracy of the activity of the plurality of muscles included in the musculoskeletal body model.

15. The apparatus according to claim 14, further comprising:
a simulation section operably connected to a processor of the one or more processors that performs a motion simulation in which a model of a body represented by the musculoskeletal body model moves, wherein the acquisition section acquires time-series data of the muscle state change that accompanies the motion according to the motion simulation.

16. The apparatus according to claim 15, wherein
the simulation section, in the simulation, moves the model of the body represented by the musculoskeletal body model according to each of a plurality of types of motion patterns, and
the acquisition section selects a motion pattern relating to the motion state that is the estimation target from among the plurality of types of motion patterns, and acquires the time-series data for the motion pattern selected from among the plurality of types of motion patterns.

17. The apparatus according to claim 14, wherein
the calculation section calculates the correlation between the sets of time-series data for each pair of muscles included among the plurality of muscles.

18. The apparatus according to claim 17, wherein
the calculation section calculates a Laplacian matrix that has rows and columns corresponding to each muscle, includes additive inverses of correlation values between a muscle corresponding to a row an a muscle corresponding to a column in off-diagonal elements, and includes total values of correlation values corresponding to the off-diagonal elements of each row or each column in on-diagonal elements.

19. The apparatus according to claim 18, wherein
the objective function includes, as an error term, a quadratic sum or a weighted quadratic sum of all elements of a vector obtained as a product of activities of the plurality of muscles and the Laplacian matrix.

20. A computer program product for estimating activity of a plurality of muscles included in a musculoskeletal body model, the computer program product comprising a non-transitory computer readable storage medium having program instructions embodied therewith, the program instructions executable by a device to cause the device to perform operations comprising:
acquiring, for each of two or more muscles included in the musculoskeletal body model, a set of time-series data of muscle state change that accompanies motion of a body;
calculating a correlation between the sets of time-series data for a pair of muscles included among the two or more muscles;
estimating joint torques based on joint angles using an inverse dynamics operation;
optimizing an objective function using the estimated joint torques; and
estimating activity of a plurality of muscles included in the musculoskeletal body model in a motion state that is an estimation target using the optimized objective function including a constraint using the correlation of the sets of time-series data to improve estimation accuracy of the activity of the plurality of muscles included in the musculoskeletal body model.

* * * * *